(12) United States Patent
Jacobson et al.

(10) Patent No.: US 10,577,677 B2
(45) Date of Patent: Mar. 3, 2020

(54) PROCESS FOR THE RECOVERY OF RARE EARTH METALS FROM PERMANENT MAGNETS

(71) Applicant: University of Houston System, Houston, TX (US)

(72) Inventors: Allan J. Jacobson, Houston, TX (US); Pradeep Samarasekere, Houston, TX (US)

(73) Assignee: University of Houston System, Houston, TX (US)

( * ) Notice: Subject to any disclaimer, the term of this patent is extended or adjusted under 35 U.S.C. 154(b) by 0 days.

(21) Appl. No.: 15/743,463

(22) PCT Filed: Jul. 11, 2016

(86) PCT No.: PCT/US2016/041685
§ 371 (c)(1),
(2) Date: Jan. 10, 2018

(87) PCT Pub. No.: WO2017/011368
PCT Pub. Date: Jan. 19, 2017

(65) Prior Publication Data
US 2018/0202025 A1   Jul. 19, 2018

Related U.S. Application Data

(60) Provisional application No. 62/191,238, filed on Jul. 10, 2015.

(51) Int. Cl.
*C22B 59/00* (2006.01)
*C22B 1/00* (2006.01)
(Continued)

(52) U.S. Cl.
CPC ............. *C22B 59/00* (2013.01); *C07F 5/003* (2013.01); *C22B 1/005* (2013.01); *C22B 3/02* (2013.01); *C22B 7/007* (2013.01); *H01F 41/0253* (2013.01); *Y02P 10/216* (2015.11); *Y02P 10/234* (2015.11)

(58) Field of Classification Search
None
See application file for complete search history.

(56) References Cited

U.S. PATENT DOCUMENTS 4,265,862 A   5/1981   White et al.
5,362,459 A   11/1994  Greenberg
(Continued)

OTHER PUBLICATIONS

Dec. 2, 2016 PCT Written Opinion and ISR.
Dec. 2, 2016 PCT Written Opinion.
Jan. 25, 2018 PCT International Preliminary Report.

*Primary Examiner* — Clinton A Brooks
(74) *Attorney, Agent, or Firm* — Carter, DeLuca & Farrell LLP; George Likourezos, Esq.

(57) ABSTRACT

Systems and methods for recovering rare earth metals from rare earth metal-containing magnets includes fragmenting or commutating the magnets, contacting the commutated magnets with a mixture of low molecular weight carboxylic acids such as formic acid and water, and removing or extracting non-rare earth metal carboxylate phases such as an iron carboxylate (formate) phase from a rare earth metal carboxylate (formate) phase, using a solvent such as water.

8 Claims, 8 Drawing Sheets

(51) Int. Cl.
*C22B 7/00* (2006.01)
*C22B 3/02* (2006.01)
*H01F 41/02* (2006.01)
*C07F 5/00* (2006.01)

(56) References Cited

U.S. PATENT DOCUMENTS

| | | |
|---|---|---|
| 8,252,085 B1 | 8/2012 | Smith et al. |
| 8,936,770 B2 | 1/2015 | Burba, III |
| 9,376,735 B2 * | 6/2016 | Jacobson ............... B09B 3/0016 |
| 2010/0031949 A1 | 12/2010 | Sugahara et al. |

* cited by examiner

SEM micrographs and EDX analysis of an as-synthesized rare earth formate crystals

PROCESS FOR THE RECOVERY OF RARE EARTH METALS FROM PERMANENT MAGNETS

RELATED APPLICATIONS

This application is a 35 U.S.C. § 371 United States National Phase Patent Application of PCT/US16/41792 filed 11 Jul. 2016, which claims priority to and the benefit of U.S. Provisional Patent Application Ser. No. 62/191,238, filed Jul. 10, 2015 (10 Jul. 2015).

BACKGROUND OF THE INVENTION

1. Field of the Invention

Embodiments of the present invention relate to systems and methods for recycling rare earth elements from end-of use products containing rare earth magnets.

More particularly, embodiments of this invention relates to systems and methods for recycling rare earth elements from end-of use products containing rare earth magnets, especially neodymium-iron-boron (NdFeB) magnets, where the methods include the steps of optionally fragmenting or commutating the magnets, contacting the commutated magnets with a mixture of formic acid and water to form rare earth metal (REM) formate precipitates ($REM(HCOO)_3$), separating the filtrate, which is impregnated with non-rare earth metal (NREM) components including iron formates ($Fe(HCOO)_2$) and borate/boric acid ($BO_3^-/H_3BO_3$) by a solid-liquid separation, and purifying the precipitated REM $(HCOO)_3$ by washing with excess water, and calcining the recovered $REM(HCOO)_3$ products to rare earth oxides ($REM_2O_3$ and $REM_6O_{11}$).

2. Description of the Related Art

NdFeB permanent magnets are fundamental components for various clean energy and high technology applications. NdFeB magnets are used, for example, in electric motors, wind turbines, missile guidance systems, hard drives, speakers, and many other existing and new technologies. The rare earth metals (REMs) in NdFeB magnets may also include, but not limited to, combinations of neodymium (Nd), praseodymium (Pr), Dysprosium (Dy), and Terbium (Tb). In some context Gadolinium (Gd) and Samarium (Sm) may also present. Nd and Dy, the primary rare earth components of NdFeB magnets are classified as two of the most critical rare earth elements in terms of supply risk and importance to advance technological fields by the U.S. Department of Energy.[1] In 2015, global demand for neodymium and dysprosium is projected to rise to 45,500 MT with an imminent supply shortage of 34,700 MT global production.[2]

Currently, the primary source for Nd and Dy are from rare earth element mining companies. The global rare earth supply, however, has not been increasing as quickly as the rise in demand due to long lead times, trade policies, environmental concerns, and other factors effecting rare earth mining. Thus, recycling of NdFeB magnets to recover Nd and Dy is considered an attractive approach to mitigate the global rare earth supply shortage. Although commercial scale waste NdFeB magnets recycling efforts are almost non-existent to date, several research projects on NdFeB magnets recycling have been reported.

Prior art and literature on methods for rare earth magnet recycling mostly comprise of hydrometallurgical methods[3] and pyrometallurgical methods.[4] Recently, hydrogen decrepitation (HD) methods,[5] gas-phase extraction methods,[6] and hydrothermal methods[7] were proposed as alternate approaches. The different recycling routes have, however, different advantages and disadvantages, described in greater detail elsewhere.[8]

Hydrometallurgical processes are by far the most common and main methods for recycling rare earths. Hydrometallurgical methods are employed mostly in commercial processes of rare earth recovery from primary mineral ores or scrap generated during the magnets manufacturing. A typical hydrometallurgical rare earth recovery process involves strong acid digestion steps which use hydrochloric acid, nitric acid or sulfuric acid to leach the rare earths, followed by a solvent extraction of the rare earth components or by a precipitation of the rare earth components using a suitable precipitating agent such as oxalate, fluoride or double salt sulfate.

The use of strong acids and the large amounts of chemicals required in hydrometallurgical processes have significant adverse environmental and economic impacts. The processes result in large amounts of liquid acid waste which causes significant waste disposal issues. During the extraction step, an excess amount, about 10 times or more of the stoichiometric amount of acid is used to enhance the stripping effect. Some of the chemicals used in the recovery processes such as fluorides, nitrates and sulfates, generate toxic, strongly oxidizing or air-polluting gases such as HF, $NO_2$, $SO_2$ and $H_2S$. From the economic perspective, obtaining high-purity single rare earth products is a common problem. In current processes co-precipitation of contaminants along with the rare earth phases is commonly observed. Most of these co-precipitated phases are not easily removable. Several other steps such as re-dissolution and re-precipitation are needed to purify the rare earth phases. The overall process is complex and multi-step resulting in longer lead times, low yields and high production costs. As a consequence it is hard to implement such methods in industrial rare earth recycling processes.

The methods disclosed in the prior art for NdFeB magnet recycling are mainly the methods for rare earth recovery from the pre-consumer production scrap or sludge. The end-of-use magnet scrap recycling is minimally researched or disclosed in the prior art. Thus, the effect of other waste materials such as the protective coating of the magnets on the recycling process is not well known. In an ideal approach, the rare earth elements need to be selectively recovered, leaving behind all the other waste materials. Given the fact that protective coating consists of nickel and copper metals, it is nearly impossible to avoid these metal ions dissolving in the leaching solution. This makes the recycling of post-consumer NdFeB magnets more complex given the need to avoid all other elements including Fe, B, Ni, and Cu in the final rare earth product.

In a previous patent application U.S. Pat. No. 9,376,735B2 issued Jun. 28, 2016 entitled "Methods and Systems for Recovering Rare Earth Elements" to Jacobson and Samarasekere, we disclosed methods and systems for recovering or extracting rare earth elements under mild conditions using a rare earth element crystallization approach. We used a crystallization medium under solvothermal conditions sufficient to form rare earth element crystals capable of gravity separation and purification. This previous invention used formamide with the addition of small amounts of formic acid and water as the dissolution and crystallization medium. Several other metals for rare earth metal recovery have been proposed such as US20110023660A1 published Feb. 3, 2011 entitled Method and Apparatus for Recovery of Rare Earth Element, US005429724A published Jul. 4, 1995 entitled Neodymium Recovery Process, and U.S. Pat. No. 6,533,837B1 issued Mar. 18, 2003 entitled Method of Recovering and Recycling Magnetic Powder from Rare Earth Bond Magnet.

While several methods have been represented above, there is a significant need for better approaches for the efficient, economical and more environmental friendly recycling of rare earth elements.

SUMMARY OF THE INVENTION

Embodiments of the present invention provide methods for recovering rare earth metals (REMs) from waste magnets comprising contacting a rare earth metal-containing magnet material with a reactant composition including a low molecular weight carboxylic acid and water under reaction conditions sufficient to dissolve or extract and concurrently precipitate rare earth metals from the rare earth metal-containing magnet material forming a precipitate including rare earth metal carboxylates and non-rare earth metal components, and removing the non-rare earth metal components from the rare earth metal carboxylates with water to form a purified rare earth metal carboxylate product.

Embodiments of the present invention provide methods for recovering rare earth metals (REMs) from rare earth containing magnets, where the methods include a reaction step, where rare earth metal containing magnets are reacted with a formic acid/water mixture to dissolve rare earth metals and non-rare earth metals from the magnets forming rare earth metal (REM) formates and non-rare earth metal (NREM) formates and/or other NREM components. The REM formate precipitates, while the NREM formates and/or other NREM components are more soluble and either remain in solution or form part of the precipitate. The methods also include filtrating the precipitates from the reaction mixture and washing the precipitate with a solvent to extract any remaining non-rare earth metal formates in the precipitate leaving a purer rare earth formate product, where the solvent is characterized in that the NREM formates and/or other NREM components are more soluble in the solvent than the REM formates. The methods of this invention are economical due to the minimum number of process steps and minimum chemical usage. As the reaction involves a metal reacting with an acid, the reaction generates a stoichiometric amount of hydrogen gas. The hydrogen gas may be disposed of by controlled burning in a combustion unit, feed to a hydrogen fuel cell for energy production, used in a hydrogenation reaction, or captured and stored for subsequent use. Thus, in certain embodiments, the hydrogen gas may be used as a fuel source to supply some or all of the energy needed to heat the reaction vessel.

The methods of this invention were successfully tested using NdFeB magnets recovered from hard disk drives, but may be used with any type of REM containing magnet products. The methods of this invention may be performed with or without any pretreatment steps, such as demagnetization or protective coating removal. Thus, the methods of this invention are simpler, less environmentally destructive or disruptive, and/or are a more economical approach for recovering rare earth elements from the REM containing magnets such as NdFeB magnets. The experiments have shown that the methods of this invention are capable of recovering at least 75% of the REMs present in the REM containing magnet materials. In certain embodiments, the recovery rate is as least 80% of the REM s present in the REM containing magnet materials. In other embodiments, the recovery rate is as least 85% of the REMs present in the REM containing magnet materials. In other embodiments, the recovery rate is as least 90% of the REMs present in the REM containing magnet materials. In other embodiments, the recovery rate is as least 95% of the REMs present in the REM containing magnet materials. Chemical analysis of the final rare earth product phases has shown that the methods of this invention are capable of recovering REM formates in greater than 90% purity, for example about 99% purity relative to the NREMs.

Embodiments of the present invention provide systems comprising a reaction vessel including a rare earth metal containing-magnet material input connect to a rare earth metal containing-magnet material source, a low molecular weight carboxylic acid input connected to a low molecular weight carboxylic acid source, a water input connected to a water source, a waste liquid outlet connected to a waste liquid receiver and a rare earth metal product outlet connected to a rare earth metal product receiver, where an amount of the rare earth metal containing-magnet material, the low molecular weight carboxylic acid and the water are added to the reaction vessel to form a reaction mixture and the reaction mixture is held under reaction conditions sufficient to dissolve or extract the rare earth metals to form rare earth metal carboxylates along with non-rare earth metal carboxylate hydrates that precipitate out of the reaction mixture, and a separating vessel to separate the precipitate from the liquid and to wash the precipitate with a solvent to remove the non-rare earth metal carboxylate hydrates to form a purified rare earth carboxylate product.

Embodiments of the present invention provide systems for recovering REMs from REM containing magnet materials, where the systems include a reaction subsystem, a separation subsystem, and extraction subsystem. The reaction subsystem includes at least one reaction vessel for contacting a REM containing magnet materials with an aqueous formic acid solution or a mixtures of formic acid and water as a reactant composition to dissolve and/or extract the REMs contained in the REM containing magnet materials. The separation subsystem includes at least one separation vessel for removing a precipitate from a liquid. The extraction subsystem includes at least one extraction vessel for removing or extracting residual NREM formates from REM formates. The systems and methods operate on the basis of the differential solubility of the REM formates compared to the NREM formates in the solvent used to remove or extract residual NREM formates from the precipitate resulting in a substantially pure REM formate product. In certain cases, the magnets are coated with a protective coating, typically a copper nickel coating comprising either layers of Cu and Ni or a Cu/Ni alloy. These coatings minimally dissolve in the formic acid/water mixture and most remain behind in the precipitate and do not appear to interfere with the extraction and/or dissolution process, but the coating pieces in the precipitate may be readily removed magnetically.

BRIEF DESCRIPTION OF THE DRAWINGS

The invention can be better understood with reference to the following detailed description together with the appended illustrative drawings in which like elements are numbered the same.

DEFINITIONS OF TERM USED IN THE INVENTION

Figure 1A:
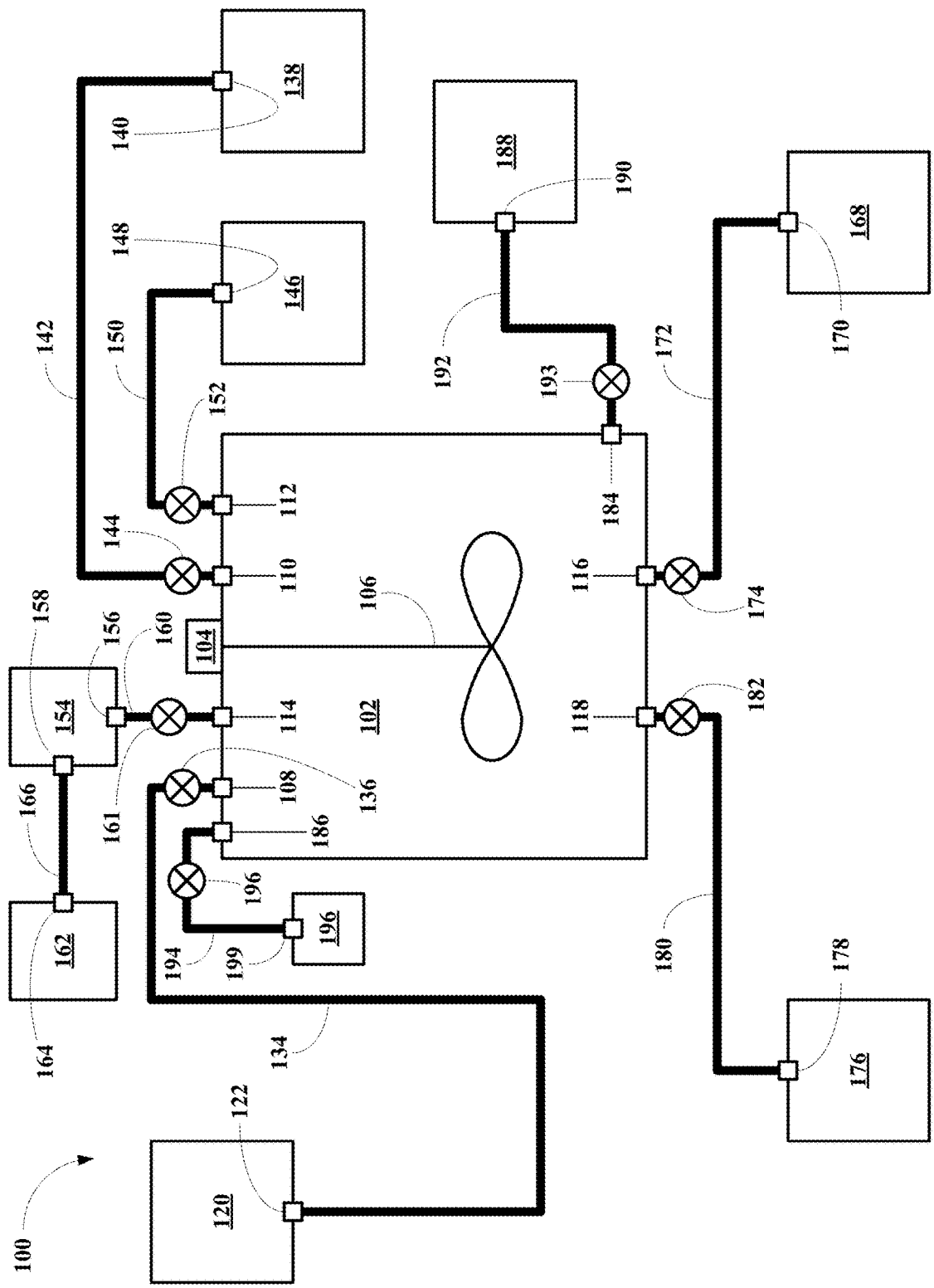
FIG. 1 depicts a first embodiment of a system of this invention.

The following definitions are provided in order to aid those skilled in the art in understanding the detailed description of the present invention.

The term "about" means that the value is within about 10% of the indicated value. In certain embodiments, the value is within about 5% of the indicated value. In certain embodiments, the value is within about 2.5% of the indicated value. In certain embodiments, the value is within about 1% of the indicated value.

The term "substantially" means that the value is within about 5% of the indicated value. In certain embodiments, the value is within about 2.5% of the indicated value. In certain embodiments, the value is within about 1% of the indicated value. In certain embodiments, the value is within about 0.5% of the indicated value. In certain embodiments, the value is within about 0.1% of the indicated value.

The term "REM" means a rare earth metal and REMs means rare earth metals selected from the group consisting of La, Ce, Pr, Nd, Sm, Eu, Gd, Tb, Dy, Ho, Er, Tm, Yb, Lu, Y, and/or Sc.

The term "w/w" means weight of magnet materials per weight of dissolving acid or weight of magnet materials to weight of water or weight of dissolving acid to weight of water.

The term "w/v" means weight of magnet material per volume of solvent.

The term "v/v" means volume of solute per volume of solvent.

The term "w/v ratio" means ratio of weight of magnet material to volume of dissolving solvent system.

The term "v/v ratio" means volume of solute to volume of solvent, here volume of water to dissolving acid.

The term "wt. %" means weight percent.

The term "vol. %" means volume percent.

DETAILED DESCRIPTION OF THE INVENTION

The inventors have found that the present systems and methods overcome the problems discussed above producing an efficient approach to recover rare earths from of rare earth metal (REM) containing magnet materials such as NdFeB waste magnet materials using an aqueous carboxylic acid solution as the only chemical reagent for dissolving out the REMs from the magnets, with or without prior pre-treatment, to form a precipitate from which residual non-rare earth metal (NREM) components are removed by solvent washing or extraction leaving a purer REM product. In the present invention, post-consumed NdFeB waste magnets were directly contacted and/or reacted with an aqueous acid solution such as an aqueous formic acid solution. The REMs were then recovered as insoluble REM carboxylates such as REM formates of the general formula REM(HCOO)$_3$. Throughout the processes, the carboxylic acid acts both as a leaching agent and a precipitating agent. The extraction and/or dissolution of REMs from the magnets and the precipitation of the REM carboxylates occur concurrently and/or simultaneously, thus the process may be classified as a one-pot synthetic approach to REM recovery from REM containing magnet materials. One especially effective carboxylic acid is formic acid also the smallest carboxylic acid. Formic acid has a low toxicity and a minimal environmental impact. By using stoichiometric amounts of formic acid to react with the REMs in the magnet materials, the amount of acid waste generated from the processes may be reduced, minimized, substantially eliminated, or completely eliminated. Besides the formation of REM and non-rare earth metal (NREM) carboxylates such as formates of iron, nickel or other transitions metals, and borates/boric acid the reaction generates stoichiometric amount of hydrogen gas (H$_2$).

In the case of the carboxylic acid being formic acid, several different REM formates have been described in the literature. Simple anhydrous REM compounds having general formula REM(HCOO)$_3$, have been known for many years and are well characterized structurally.[9] The compounds have a neutral framework structure composed of REM$^{3+}$ ions coordinated by the oxygen atoms of the formate ligands. The REM$^{3+}$ ions are coordinated by nine oxygen atoms in a tricapped trigonal prismatic geometry. The oxygen atoms of the formate ligand differ; one forms $\mu^2$-bridges between neighboring REM$^{3+}$ ions, while the second is mono-coordinating. The space group is non-centric.

The reactant compositions of the present invention comprise an aqueous solution of formic acid or other low molecular weight carboxylic acid. The reaction is characterized by the following reactions of formic acid and REMs:

REM+3RCOOH ➔ REM(RCOO)$_3$+(3/2)H$_2$

NREM+nRCOOH ➔ NREM(RCOO)$_n$+(n/2)H$_2$ where REM is a rare earth metal, R is a hydrogen atom or an alkyl group having between 1 and 3 carbon atoms, and n is an integer having value between 2 and 3. In certain embodiments, the REM is Nd and the NREM is Fe and R is a hydrogen atom and n is 2. As the reaction generation stoichiometric amount of hydrogen gas, the hydrogen gas may be disposed of by controlled burning in a combustion unit, feed to a hydrogen fuel cell for energy production, used in hydrogenation reaction, or captured and stored for subsequent use. Thus, in certain embodiments, the hydrogen gas may be used as a fuel source to supply some or all of the energy needed to heat the reaction to vessel.

The reaction mixture may be characterized by two ratio: a ratio of magnet material to formic acid and a ratio of formic acid to water or by a single ratio of magnet material to formic acid to water. These ratio are best expressed on a w/w basis. The stoichiometric reactant ratios may be calculated by assuming an irreversible reaction. Based on the balanced equation, the theoretical ratio of magnet materials to formic acid may be calculated as 1:1.44 w/w. Based on the solubility data of Fe(HCOO)$_2$.2H$_2$O at 25° C., the theoretical amount of water required to dissolve all the Fe (HCOO)$_2$.2H$_2$O can be calculated as 1:30 w/w magnet materials to water. Thus, the ratio of magnetic material to formic acid to water is 1:1.44:30 w/w. In general operation, the ratio of magnet material to formic acid to water is between about 1:1:20 w/w to about 1:2:50 w/w. In other embodiments, the magnet material to formic acid to water ratio is between about 1:1.2:20 w/w and about 1:1.8:50 w/w. In other embodiments, the magnet material to formic acid to water ratio is between about 1:1.3:20 w/w and about 1:1.6:50 w/w. In other embodiments, the magnet material to formic acid to water ratio is between about 1:1.4:20 w/w and about 1:1.5:50 w/w. In other embodiments, the magnet material to formic acid to water ratio is between about 1:1.4:20 w/w and about 1:1.5:40 w/w.

Reaction Conditions of the Invention

The parameters or reaction conditions used in the examples of the reaction processes of this invention including at least reaction temperature, reaction pressure, reaction time, and stirring rate. In general, the reaction temperature is between about 25° C. and about 120° C. In certain embodiments, the reaction temperature may be any discrete temperature in the range between about 25° C. and about 120° C. In other embodiments, the reaction temperature may be selected from the group of selected from 25° C., 50° C., 75° C., 100° C., and 120° C. In general, the reaction pressure is between about 1 atmosphere and about 5 atmospheres. In other embodiments, the reaction pressure is between about 1 atmosphere and 2 atmospheres. In other embodiments, the pressure is ambient pressure. In general, the reaction time is up to 24 hours or more. In certain embodiments, the reaction time is between about 3 hours and 24 hours. In other embodiments, the reaction time is any discrete time period in the range between 3 hours and 24 hours. In other embodiments, the reaction time is selected from the group consisting of 3 hours, 6 hours, 9 hours, 12 hours, 15 hours, 18 hours, 21 hours, and 24 hours. In general, the rate of stirring is up to 500 rpm or more. In other embodiments, the stirring rate is between about 100 rpm and 500 rpm. In other embodiments, the reaction time is any discrete stirring rate in the range between 100 rpm and 500 rpm. In other embodiments, the stirring rate is selected from the group consisting of 100 rpm, 150 rpm, 200 rpm, 250 rpm, 300 rpm, 350 rpm, 400 rpm, 450 rpm, and 500 rpm.

Once the rare earth metals are separated as $REM(HCOO)_3$ product, the precipitate may be converted to economically valuable mixed rare earth oxides through a calcination step. The calcination may be performed by heating $REM(HCOO)_3$ product to a calcination temperature in the range between about 750° C. and about 1,000° C. for a calcination time between about 3 hours and about 5 hours.

It should also be noted that the invention may also be applied to the recovery of REMs from other REM magnet materials including, but not limited to, Samarium-Cobalt (Sm—Co) magnet materials.

Suitable Reagents and Components of the Invention

Suitable reagent used for this processes of this invention include low molecular weight carboxylic acids of the general formula RCOOH or R—C(O)—OH, where R is H or an alkyl group having between 1 and 3 carbon atoms. Exemplary examples include, without limitation, formic acid ($HCOOH$ or H—C(O)—OH) representing the smallest member of the carboxylic acids useful in the present invention, acetic acid ($CH_3COOH$ or $CH_3$—C(O)—OH), propanoic acid ($CH_3CH_2COOH$ or $CH_3CH_2$—C(O)—OH), other low molecular weight carboxylic acids, or mixtures and combinations thereof. Formic acid is a weak organic acid and is considered to be a reagent having low toxicity and environmentally friendly solvent due to its low environmental impact. Due to its relatively high hydrogen content, formic acid has been proposed as a valuable, safe and economical hydrogen carrier. Formic acid may be catalytically decomposed to yield hydrogen and carbon dioxide, while in the present invention, the reaction are controlled to yield metal formates and hydrogen gas. Under proper reaction conditions formic acid ionizes to formate anions ($HCO_2^-$ or H—C(O)—O$^-$) and hydrogen ions ($H^+$). In this invention, we disclose the use of formic acid as an effective reagent for the recovery of rare earth components from magnets such as NdFeB magnets as rare earth formates of the structure ($REM(HCOO)_3$).

Suitable rare earth metals (REMs) to be extracted by the methods and systems of this invention include, without limitation, Lanthanum (La), Cerium (Ce), praseodymium (Pr), neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu), and mixtures or combinations thereof.

Suitable non-rare earth metals or elements (NREMs) to be extracted by the methods and systems of this invention include, without limitation, iron (Fe), nickel (Ni), copper (Cu), boron (B) other transitions metals generally associated with materials that include REMs, and mixtures or combinations thereof.

DETAILED DESCRIPTION OF THE SYSTEM AND METHOD FIGURES

First Embodiment

Referring now to FIG. 1A, a first embodiment of system of this invention, generally 100, is shown to include a heated reaction vessel 102 including a motor 104 and a paddle stirrer 106. The reaction vessel 102 also includes a REM containing magnet material inlet 108, a water inlet 110 and a formic acid inlet 112. The reaction vessel 102 also includes a gas outlet 114, a waste liquid outlet 116 and a REM product outlet 118.

The system 100 also includes a REM containing magnet material source vessel 120 having a REM containing magnet material outlet 122. The outlet 122 is connected to the inlet 108 via a REM containing magnet material conduit 134 having a REM containing magnet material conduit valve 136.

The system 100 also includes a water source vessel 138 having a water outlet 140. The water outlet 140 is connected to the water inlet 110 via a water conduit 142 having a water conduit valve 144. The system 100 also includes a formic acid source vessel 146 having a formic acid outlet 148. The formic acid outlet 148 is connected to the formic acid inlet 112 via a formic acid conduit 150 including a formic acid conduit valve 152.

The system 100 also includes a hydrogen gas bubbler 154 having a hydrogen gas inlet 156 and a hydrogen gas outlet 158, where the gas outlet 114 is connected to the hydrogen gas inlet 156 via a hydrogen gas conduit 160 having a hydrogen gas valve 161. The system 100 also includes a hydrogen gas utilization or storage unit 162 having a hydrogen gas inlet 164 connected to the hydrogen gas outlet 158 via a second hydrogen gas conduit 166. In certain embodiments, the hydrogen gas utilization or storage unit 164 may be a combustor, where the heat produced may be used to heat the reaction vessel 102 to a desired elevated temperature. In other embodiments, the hydrogen gas utilization or storage unit 162 may be a hydrogen fuel cell for generating electrical power that may be used to heat the reaction vessel 102 or to power the reaction controllers and other electrical equipment associated with the systems. In other embodiments, the hydrogen gas utilization or storage unit 164 may be a hydrogen gas storage vessel, where the hydrogen gas is stored for latter use such as combustion in combustors or fuel cells or in hydrogenation reactions or in any other process that uses hydrogen gas as a reagent.

The system 100 also includes a waste liquid vessel 168 having a waste liquid inlet 170, where the waste liquid outlet 116 is connected to the waste liquid inlet 170 via a waste liquid conduit 172 having a waste liquid conduit valve 174. The system 100 also includes a rare earth product vessel 176 having a rare earth product inlet 178, where the rare earth product outlet 118 is connected to the rare earth product inlet 178 via a rare earth conduit 180 having a rare earth conduit valve 182.

The system 100 operates as follows. Rare earth containing HDD magnets are loaded into the vessel 120. The valve 132 is opened and the magnets enter the commutating unit 124, where the magnets are commutated into a particulate magnet input material. The commutating may be accomplished by grinding, cryogenic grinding, pressure fracturing, shredding, any other commutating technique or mixtures and combinations thereof. The valve 136 is opened and the particulate magnetic input material is supplied to the reactor vessel 102. Once a desired amount of the input material is added to the reactor 102, the valve 136 is closed and a mixture of water and formic acid is added to the reactor 102, where the relative amount of water and formic acid are controlled by the valves 144 and 152. Once the designated amount of water and formic acid are added, the valves 144 and 152 are closed. The reaction vessel 102 is stirred and maintained at a temperature of about 100° C. Gas evolved during the reaction exits the reaction vessel 102 into the hydrogen gas bubbler 154. After the desired reaction time, waste liquid is withdrawn from the reaction vessel 102, by opening the valve 174 into the waste liquid vessel 168. After the waste liquid is removed, the valve 174 is closed. The solids in the reaction vessel 102 are washed with water by open the water valve 144 until substantially all or all non-rare earth precipitate is dissolved by the added water. Once the non-rare earth precipitate has been dissolved away, the water valve 144 is closed and the rare earth product valve 182 is opened transferring the product into the product vessel 176. Thus, the major part of the reaction occurs in the reaction vessel 102. The generated hydrogen gas proceeds through the bubbler 154 and into the hydrogen gas utilization or storage vessel 162.

In certain embodiments, the reaction vessel 102 will be purged with an inert gas such as nitrogen, argon, methane, hydrogen, or mixtures and combinations thereof to remove unwanted oxygen gas to minimize metal oxidation especially iron oxidation to the ferric oxidation state. Thus, the reaction vessel 102 may further includes an inert gas inlet 184 and a purge gas outlet 186. The reactor vessel 102 also includes an inert gas vessel 188 having an inert gas outlet 190 connected to the inert gas inlet 184 via an inert gas conduit 192 having a inert gas valve 193. The inert gas fed into the reactor vessel 102 passes through the reaction medium removing unwanted gases and exits the reactor vessel 102 through the purge outlet 186 through a purge conduit 194 having a purge valve 196 into a purge vent 198 having an inlet 199. The inert gas may be used at different stages of the reaction to purge gases from the reaction medium.

Second Embodiment

Figure 1B:
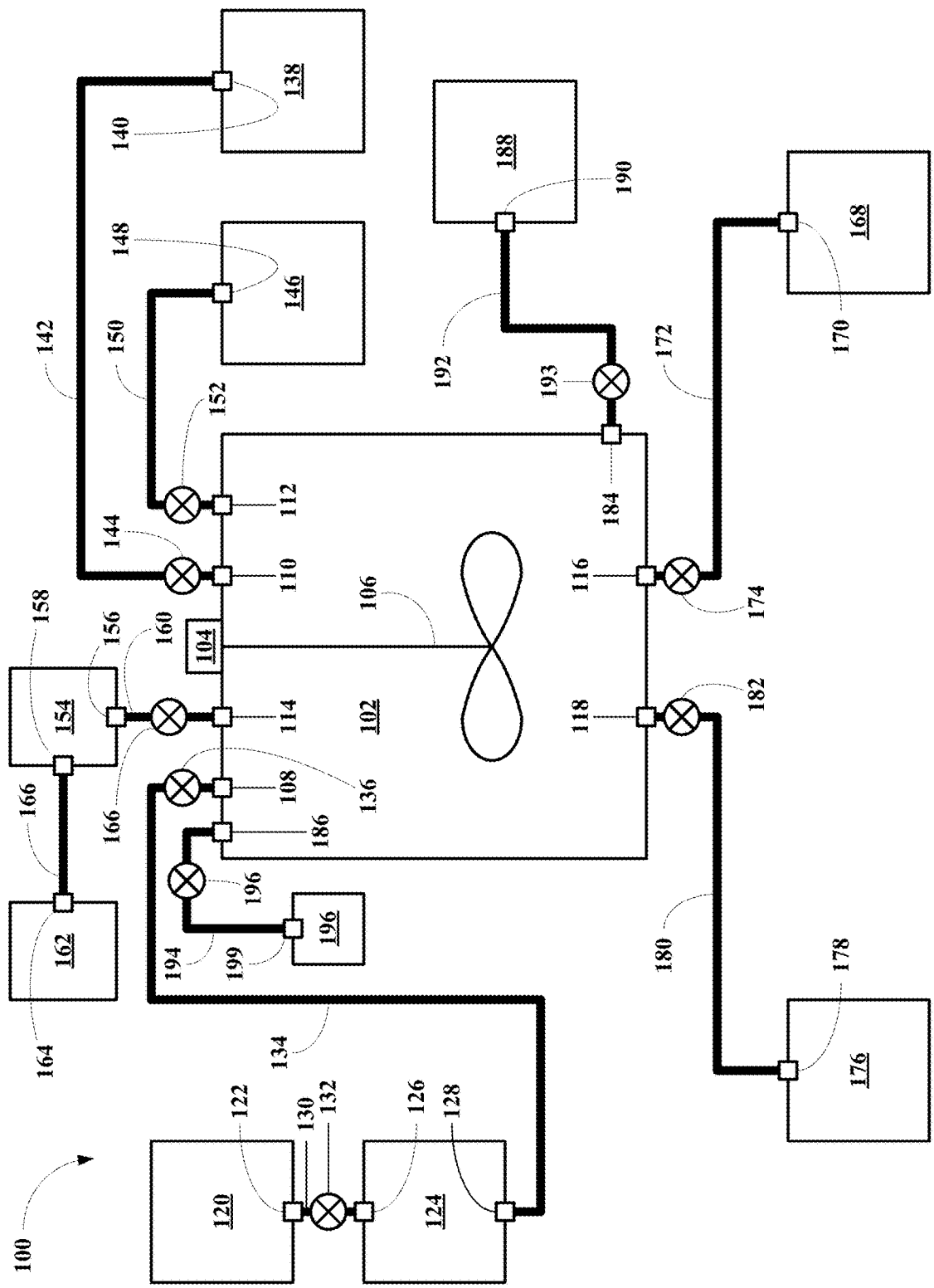

Referring now to FIG. 1B, a first embodiment of system of this invention, generally 100, is shown to include a heated reaction vessel 102 including a motor 104 and a paddle stirrer 106. The reaction vessel 102 also includes a particulate REM containing magnet material inlet 108, a water inlet 110 and a formic acid inlet 112. The reaction vessel 102 also includes a gas outlet 114, a waste liquid outlet 116 and a REM product outlet 118.

The system 100 also includes a REM containing magnet material source vessel 120 having a REM containing magnet material outlet 122. The system 100 also includes a commutating unit 124 having a REM containing magnet material inlet 126 and a particulate REM containing magnet material outlet 128. The REM containing magnet material outlet 122 is connected to the magnet inlet 126 via a magnet conduit 130 having a magnet conduit valve 132. The particulate magnet outlet 128 is connected to the particulate magnet inlet 108 via a particulate magnet conduit 134 having a particulate magnet conduit valve 136.

The system 100 also includes a water source vessel 138 having a water outlet 140. The water outlet 140 is connected to the water inlet 110 via a water conduit 142 having a water conduit valve 144. The system 100 also includes a formic acid source vessel 146 having a formic acid outlet 148. The formic acid outlet 148 is connected to the formic acid inlet 112 via a formic acid conduit 150 including a formic acid conduit valve 152.

The system 100 also includes a hydrogen gas bubbler 154 having a hydrogen gas inlet 156 and a hydrogen gas outlet 158, where the gas outlet 114 is connected to the hydrogen gas inlet 156 via a hydrogen gas conduit having a hydrogen gas valve 161. The system 100 also includes a hydrogen gas utilization or storage unit 162 having a hydrogen gas inlet 164 connected to the hydrogen gas outlet 158 via a second hydrogen gas conduit 166. In certain embodiments, the hydrogen gas utilization or storage unit 162 may be a combustor, where the heat produced may be used to heat the reaction vessel 102 to a desired elevated temperature. In other embodiments, the hydrogen gas utilization or storage unit 162 may be a hydrogen fuel cell for generating electrical power that may be used to heat the reaction vessel 102 or to power the reaction controllers and other electrical equipment associated with the systems. In other embodiments, the hydrogen gas utilization or storage unit 162 may be a hydrogen gas storage vessel, where the hydrogen gas is stored for latter use such as combustion in combustors or fuel cells or in hydrogenation reactions or in any other process that uses hydrogen gas as a reagent.

The system 100 also includes a waste liquid vessel reaction vessel 168 having a waste liquid inlet 170, where the waste liquid outlet 116 is connected to the waste liquid inlet 170 via a waste liquid conduit 172 having a waste liquid conduit valve 174. The system 100 also includes a rare earth product vessel 176 having a rare earth product inlet 178, where the rare earth product outlet 118 is connected to the rare earth product inlet 178 via a rare earth conduit 180 having a rare earth conduit valve 182.

The system 100 operates as follows. REM containing HDD magnets are loaded into the vessel 120. The valve 132 is opened and the magnets enter the commutating unit 124, where the magnets are commutated into a particulate magnet input material. The commutating may be accomplished by grinding, cryogenic grinding, pressure fracturing, shredding, any other commutating technique or mixtures and combinations thereof. The valve 136 is opened and the particulate magnetic input material is supplied to the reactor vessel 102. Once a desired amount of the input material is added to the reactor 102, the valve 136 is closed and a mixture of water and formic acid is added to the reactor 102, where the relative amount of water and formic acid are controlled by the valves 144 and 152. Once the designated amount of water and formic acid are added, the valves 144 and 152 are closed. The reaction vessel 102 is stirred and maintained at a temperature of about 100° C. Gas evolved during the reaction exits the reaction vessel 102 into the hydrogen gas bubbler 154. After the desired reaction time, waste liquid is withdrawn from the reaction vessel 102, by opening the valve 174 into the waste liquid vessel 168. After the waste liquid is removed, the valve 174 is closed. The solids in the reaction vessel 102 are washed with water by open the water valve 144 until substantially all or all non-rare earth precipitate is dissolved by the added water. Once the non-rare earth precipitate has been dissolved away, the water valve 144 is closed and the rare earth product valve 182 is opened transferring the product into the product vessel 176. Thus, the major part of the reaction occurs in the reaction vessel 102. The generated hydrogen gas proceeds through the bubbler 154 and into the hydrogen gas utilization or storage vessel 162.

In certain embodiments, the reaction vessel 102 will be purged with an inert gas such as nitrogen, argon, methane, hydrogen, or mixtures and combinations thereof to remove unwanted oxygen gas to minimize metal oxidation especially iron oxidation to the ferric oxidation state. Thus, the reaction vessel 102 may further includes an inert gas inlet 184 and a purge gas outlet 186. The reactor vessel 102 also includes an inert gas vessel 188 having an inert gas outlet 190 connected to the inert gas inlet 184 via an inert gas conduit 192 having a inert gas valve 193. The inert gas fed into the reactor vessel 102 passes through the reaction medium removing unwanted gases and exits the reactor vessel 102 through the purge outlet 186 through a purge conduit 194 having a purge valve 196 into a purge vent 198 having an inlet 199. The inert gas may be used at different stages of the reaction to purge gases from the reaction medium.

Third Embodiment

Figure 2:
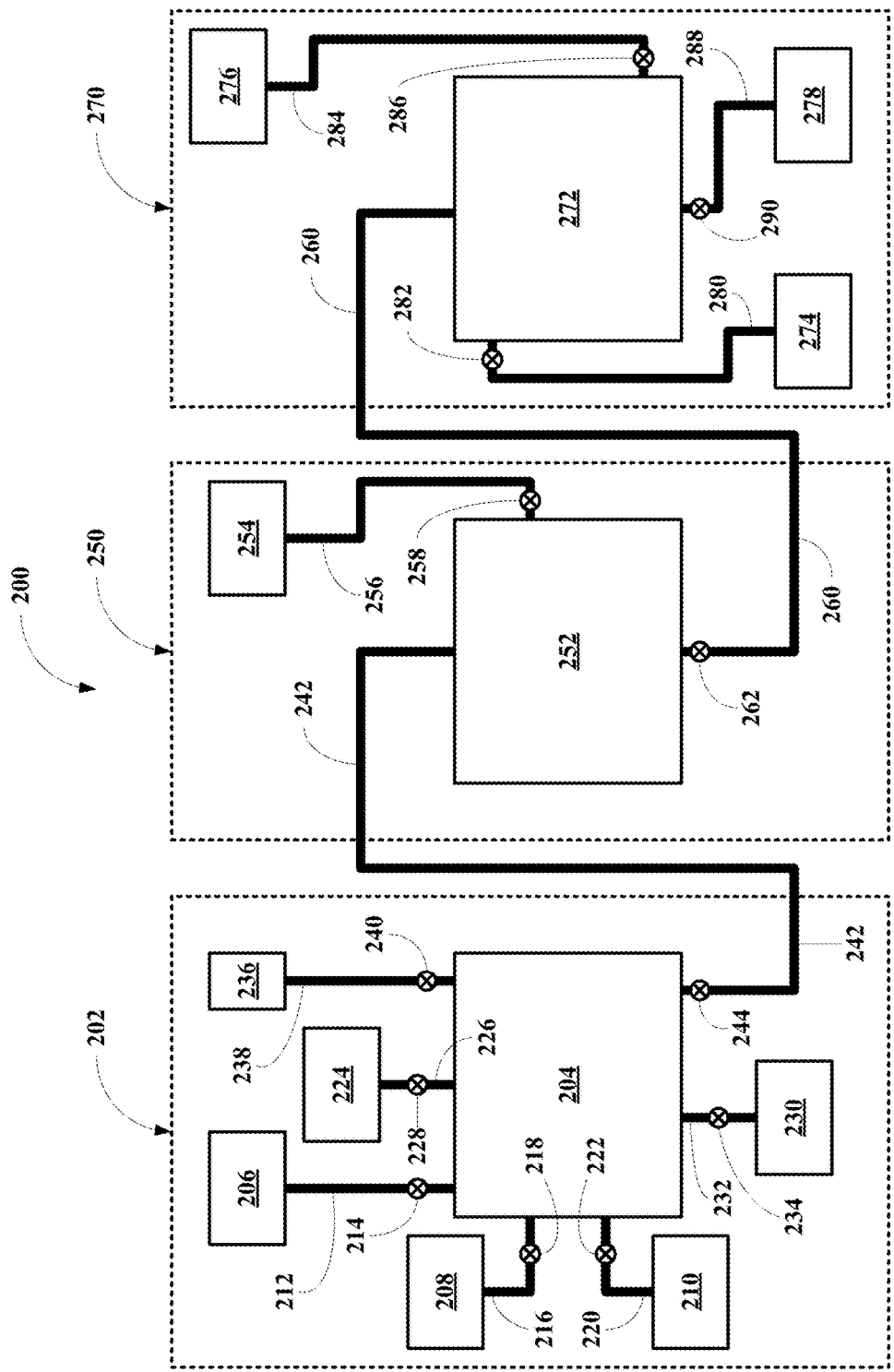
FIG. 2 depicts a second embodiment of a system of this invention.

Referring now to FIG. 2, a first embodiment of system of this invention, generally 200, is shown to include a reaction subsystem 202, a separation subsystem 250, and an extraction subsystem 270.

Reaction Subsystem

The reaction subsystem 202 includes a single reaction vessel 204, a REM containing magnet material source vessel 206, a formic acid source vessel 208, and a water source vessel 210. The magnet material source vessel 206 is connected to the reaction vessel 204 via a magnet material conduit 212 having a magnet material valve 214. The formic acid source vessel 208 is connected to the reaction vessel 204 via a formic aid conduit 216 having a formic acid valve 218. The water source vessel 210 is connected to the reaction vessel 204 via a water conduit 220 having a water valve 222. The reaction vessel 204 also includes a hydrogen gas utilization unit 224 connected to the reaction vessel 204 via a hydrogen gas conduit 226 having a hydrogen gas valve 228. The reaction vessel 204 also includes an inert gas source 230 connected to the reaction vessel 204 via an inert gas conduit 232 having an inert gas valve 234. The reaction vessel 204 also includes a purge gas vent 236 connected to the reaction vessel 204 via a purge gas conduit 238 having a purge gas valve 240. The reaction vessel 204 also includes a reaction mixture conduit 242 having a reaction mixture valve 244.

Separation Subsystem

The separation subsystem 250 is shown here to comprise a single separation vessel 252 and a liquid receiving vessel 254. The reaction mixture conduit 242 connects the reaction vessel 204 and the separation vessel 252 and is used to transport the reaction mixture from the reaction vessel 204 to the separation vessel 252. The separation vessel 252 is connected to the liquid receiving vessel 254 via a liquid conduit 256 having a liquid valve 258. The separation vessel 252 also includes a solids conduit 260 having a solids valve 262.

Extraction Subsystem

The extraction subsystem 270 is shown here to comprise a single extraction vessel 272, a solvent source vessel 274, a liquid vessel 276, and a product vessel 278. The solids conduit 260 connects the separation vessel 252 and the extraction vessel 272 and is used to transport the solids from the separation vessel 252 to the extraction vessel 272. The separation vessel 272 is connected to the solvent source vessel 274 via a solvent conduit 280 having a solvent valve 282. The separation vessel 272 is also connected to the liquid vessel 276 via a liquid conduit 284 having a liquid valve 286. The separation vessel 272 is also connected to the product vessel 274 via a product conduit 288 having a product valve 290.

Fourth Embodiment

Figure 3:
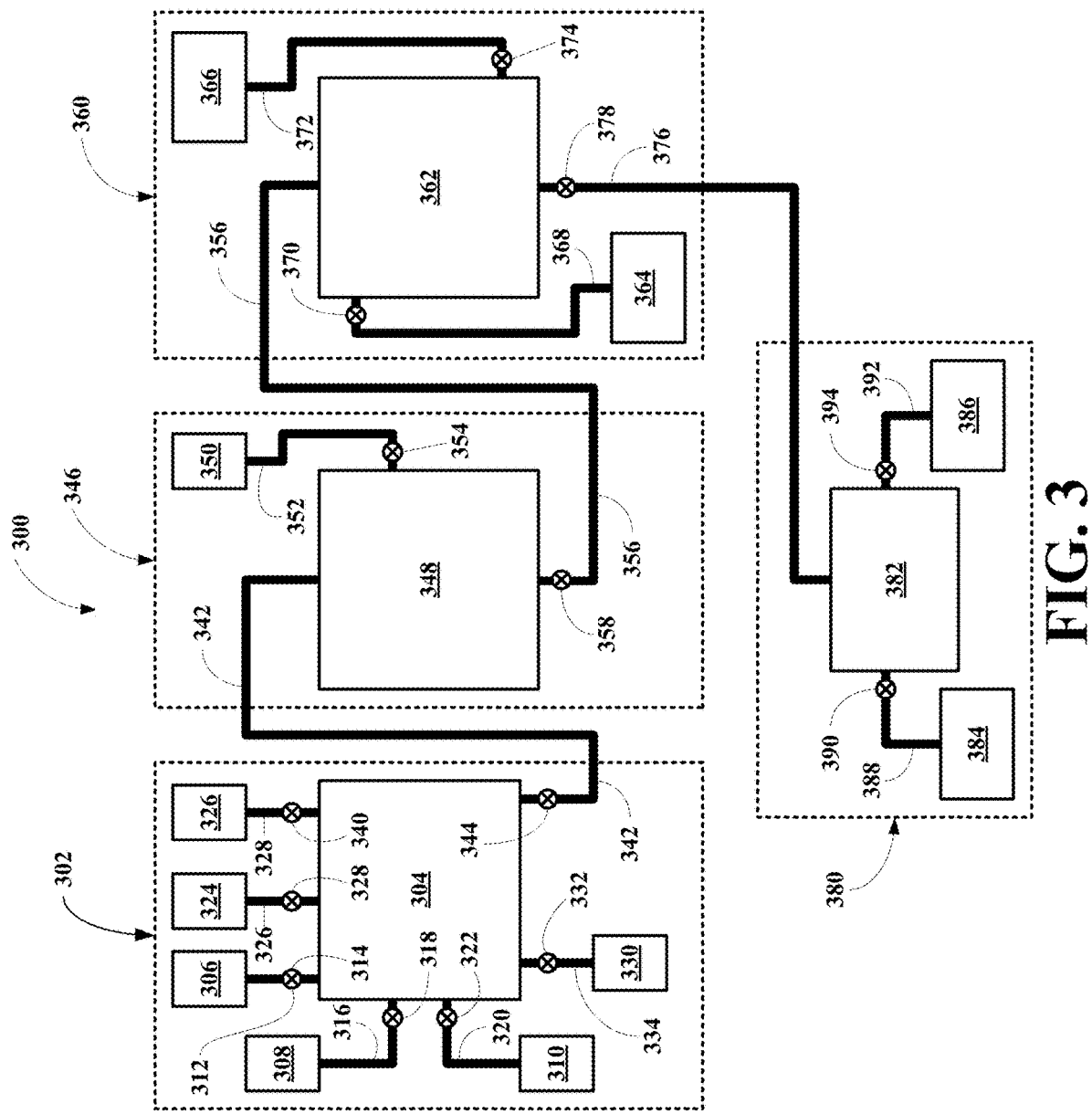
FIG. 3 depicts a third embodiment of a system of this invention.

Referring now to FIG. 3, a second embodiment of system of this invention, generally 300, is shown to include a reaction subsystem 302, a separation subsystem 346, an extraction subsystem 350, and a recovery and recycle subsystem 380.

Reaction Subsystem

The reaction subsystem 302 includes a single reaction vessel 304, a magnet source vessel 306, a formic acid source vessel 308, and a water source vessel 310. The magnet source vessel 306 is connected to the reaction vessel 304 via a magnet conduit 312 having a magnet valve 314. The formic acid source vessel 308 is connected to the reaction vessel 304 via a formic aid conduit 316 having a formic acid valve 318. The water source vessel 310 is connected to the reaction vessel 304 via a water conduit 320 having a water valve 322. The reaction vessel 304 also includes a hydrogen gas utilization unit 324 connected to the reaction vessel 304 via a hydrogen gas conduit 326 having a hydrogen gas valve 328. The reaction vessel 304 also includes an inert gas source 330 connected to the reaction vessel 304 via an inert gas conduit 332 having an inert gas valve 334. The reaction vessel 304 also includes a purge gas vent 336 connected to the reaction vessel 304 via a purge gas conduit 338 having a purge gas valve 340. The reaction vessel 304 also includes a reaction mixture conduit 342 having a reaction mixture valve 344.

Separation Subsystem

The separation subsystem 346 is shown here to comprise a single separation vessel 348 and a liquid receiving vessel 350. The reaction mixture conduit 342 connects the reaction vessel 304 and the separation vessel 348 and is used to transport the reaction mixture from the reaction vessel 304 to the separation vessel 348. The separation vessel 352 is connected to the liquid receiving vessel 350 via a liquid conduit 352 having a liquid valve 354. The separation vessel 352 also includes a solids conduit 356 having a solids valve 358.

Extraction Subsystem

The extraction subsystem 360 is shown here to comprise a single extraction vessel 362, a solvent source vessel 364, and a liquid vessel 366. The solids conduit 356 connects the separation vessel 348 and the extraction vessel 262 and is used to transport the solids from the separation vessel 348 to the extraction vessel 362. The separation vessel 362 is connected to the solvent source vessel 364 via a solvent conduit 368 having a solvent valve 370. The separation vessel 362 is also connected to the liquid vessel 366 via a liquid conduit 372 having a liquid valve 374. The separation vessel 262 is also includes a product conduit 376 having a product valve 378.

Recovery and Recycle Subsystem

The recovery and recycle subsystem 380 is shown here to comprise a single a recovery and recycle vessel 382, a recycle formic acid vessel 384, and a rare earth metal product vessel 386. The recovery and recycle vessel 382 is connected to the recycle formic acid vessel 384 via a recycle formic acid conduit 388 having a recycle formic acid valve 390. The recovery and recycle vessel 382 is connected to the rare earth metal product vessel 386 via a rare earth metal product conduit 392 having a product valve 394.

Fifth Embodiment

Figure 4:
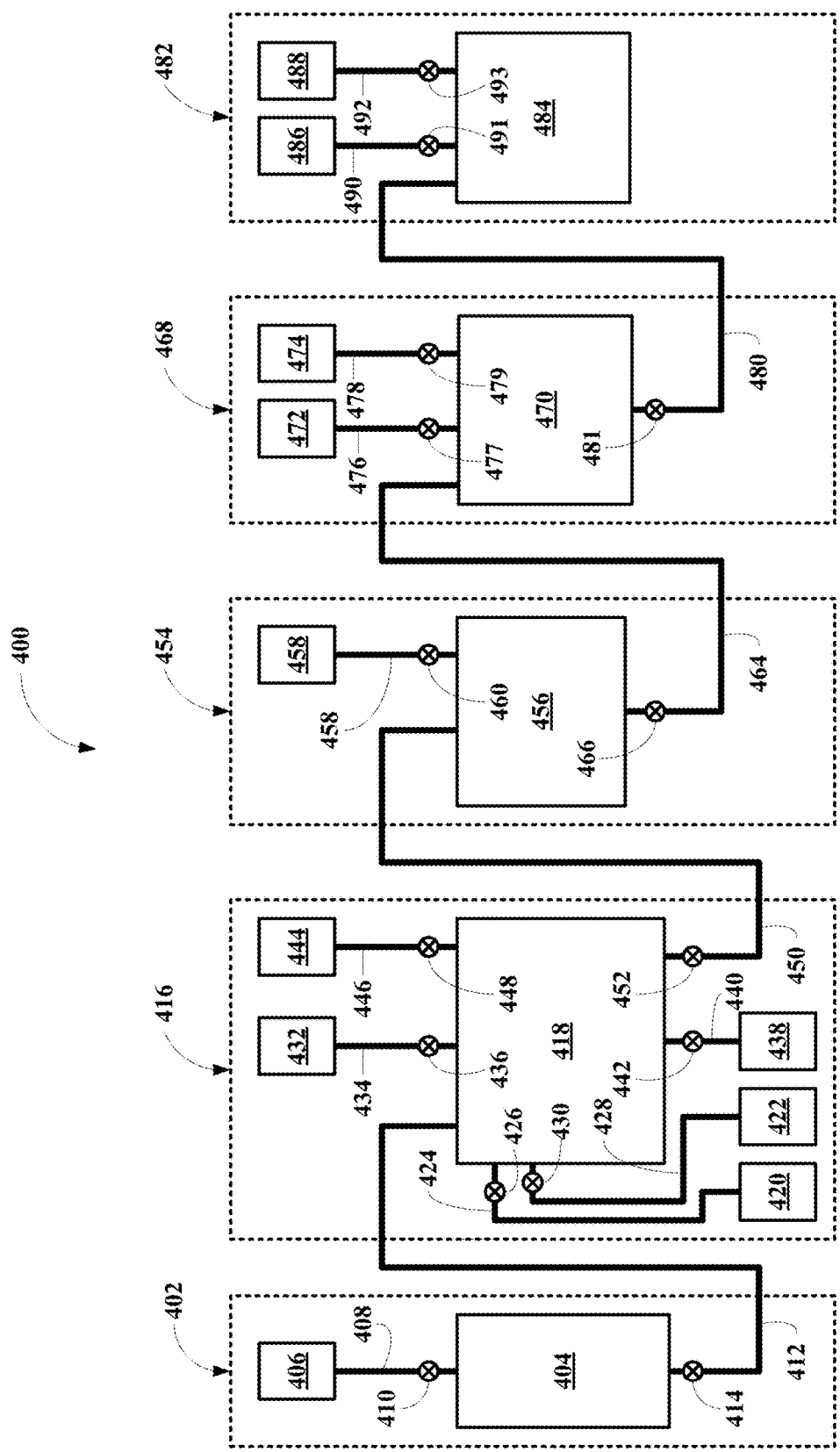
FIG. 4 depicts a fourth embodiment of a method of this invention.

Referring now to FIG. 4, a third embodiment of system of this invention, generally 400, is shown to include a commutating subsystem 402, a reaction subsystem 416, a separation subsystem 438, an extraction subsystem 454, and a recovery and recycle subsystem 476.

Commutating Subsystem

The commutating subsystem 402 includes a commutating unit 404 and a magnet source vessel 406. The magnet source vessel 406 is connected via a magnet source conduit 408 having a magnetic source valve 410. The commutating unit 404 also includes a particulate magnet material conduit 412 having a particulate magnet valve 414.

Reaction Subsystem

The reaction subsystem 416 includes a single reaction vessel 418, a formic acid source vessel 420, and a water source vessel 422. The commutating unit 404 is connected to the reaction vessel 404 via the particulate magnet conduit 414. The formic acid source vessel 420 is connected to the reaction vessel 418 via a formic aid conduit 424 having a formic acid valve 426. The water source vessel 422 is connected to the reaction vessel 418 via a water conduit 428 having a water valve 430. The reaction subsystem 416 also includes a hydrogen gas utilization unit 432 connected to the reaction vessel 418 via a hydrogen gas conduit 434 having a hydrogen gas valve 436. The reaction subsystem 416 also includes an inert gas source 438 connected to the reaction vessel 418 via an inert gas conduit 440 having an inert gas valve 442. The reaction subsystem 416 also includes a purge gas vent 444 connected to the reaction vessel 418 via a purge gas conduit 446 having a purge gas valve 448. The reaction vessel 418 also includes a reaction mixture conduit 450 having a reaction mixture valve 452.

Separation Subsystem

The separation subsystem 454 is shown here to comprise a single separation vessel 456 and a liquid receiving vessel 458. The reaction mixture conduit 450 connects the reaction vessel 418 and the separation vessel 456 and is used to transport the reaction mixture from the reaction vessel 418 to the separation vessel 454. The separation vessel 456 is connected to the liquid receiving vessel 458 via a liquid conduit 460 having a liquid valve 462. The separation vessel 456 also includes a solids conduit 464 having a solids valve 466.

Extraction Subsystem

The extraction subsystem 468 is shown here to comprise a single extraction vessel 470, a solvent source vessel 472, and a liquid vessel 474. The solids conduit 464 connects the separation vessel 456 and the extraction vessel 470 and is used to transport the solids from the separation vessel 456 to the extraction vessel 470. The separation vessel 470 is connected to the solvent source vessel 472 via a solvent conduit 476 having a solvent valve 477. The separation vessel 470 is also connected to the liquid vessel 474 via a liquid conduit 478 having a liquid valve 479. The separation vessel 470 also includes a product conduit 480 having a product valve 481.

Recovery and Recycle Subsystem

The recovery and recycle subsystem 482 is shown here to comprise a single a recovery and recycle vessel 484, a recycle formic acid vessel 486, and a rare earth metal product vessel 488. The product conduit 480 connects the extraction vessel 470 to the recovery and recycle vessel 484 and is sued to transport the product to the recovery and recycle vessel 484. The recovery and recycle vessel 484 is connected to the recycle formic acid vessel 486 via a recycle formic acid conduit 490 having a recycle formic acid valve 491. The recovery and recycle vessel 488 is connected to the rare earth metal product vessel 488 via a rare earth metal product conduit 492 having a product valve 493.

EXPERIMENTS OF THE INVENTION

The present invention is illustrated by the following examples:

The NdFeB magnets were obtained from discarded hard disk drives (HDDs). The HDDs were disassembled manually and 2 to 4 magnets were collected from each HDD. Weights of the magnets ranged from about 2.5 g to about 10 g. The NdFeB magnets used for the reactions were pretreated. However, the NdFeB magnets may be used as-removed without any pretreatment. The term "pretreatment" refers hereto, but not limited to, demagnetization, roasting, and/or protective coating removal. The magnets were crushed into small pieces using a metal crusher. The brittle magnets are easily breakable into pieces, but any commutating method may be used including grinding, milling, crushing, external pressing, etc. The particle sizes varied in a broad range between about 10 nm and about 5 mm. The crushed magnet sample was reacted with a mixture of formic acid and water or an aqueous formic acid solution. In certain embodiments, the particle sizes range between about 100 nm (0.1 µm) to about 5 mm. In other embodiments, the particle sizes range between about 500 nm (0.5 µm) to about 5 mm. In other embodiments, the particle sizes range between about 1 µm to about 5 mm. In other embodiments, the particle sizes range between about 5 µm to about 5 mm. In other embodiments, the particle sizes range between about 10 µm to about 5 mm. In other embodiments, the particle sizes range between about 100 µm to about 5 mm. In other embodiments, the particle sizes range between about 500 µm to about 5 mm.

Example 1

Figure 5:
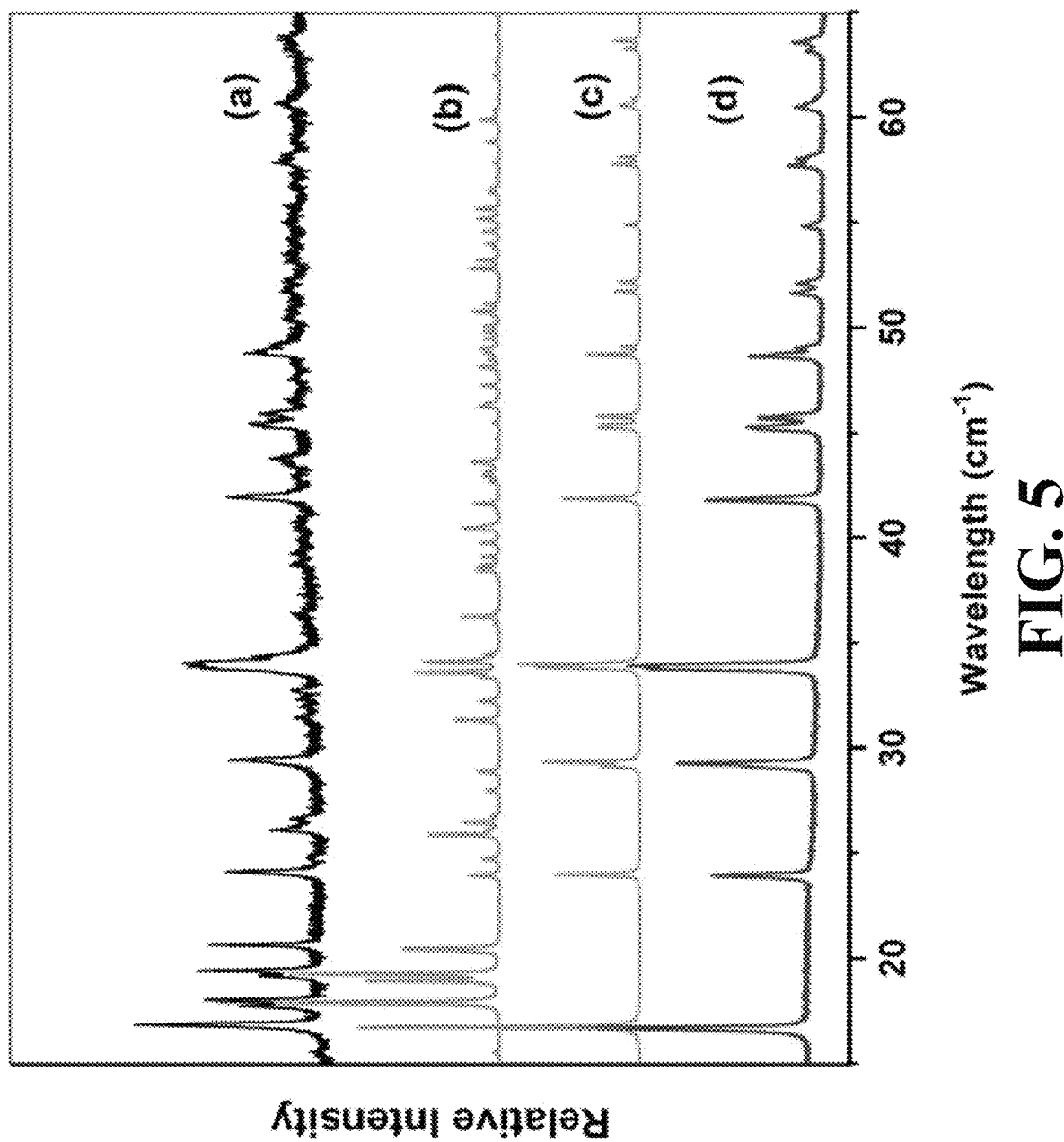
FIG. 5 depicts powder X-ray patterns (PXRD) of (a) as synthesized solid product of the reaction. Solid phase consists of a mixture of REM(HCOO)$_3$, where REM is a rare earth metal, and Fe(HCOO)$_2$.2H$_2$O; (b) simulated PXRD pattern of Fe(HCOO)$_2$.2H$_2$O; (c) simulated PXRD pattern of Nd(HCOO)$_3$; and (d) nearly-pure REM(HCOO)$_3$ phase after Fe(HCOO)$_2$.2H$_2$O removal.
Figure 6A:
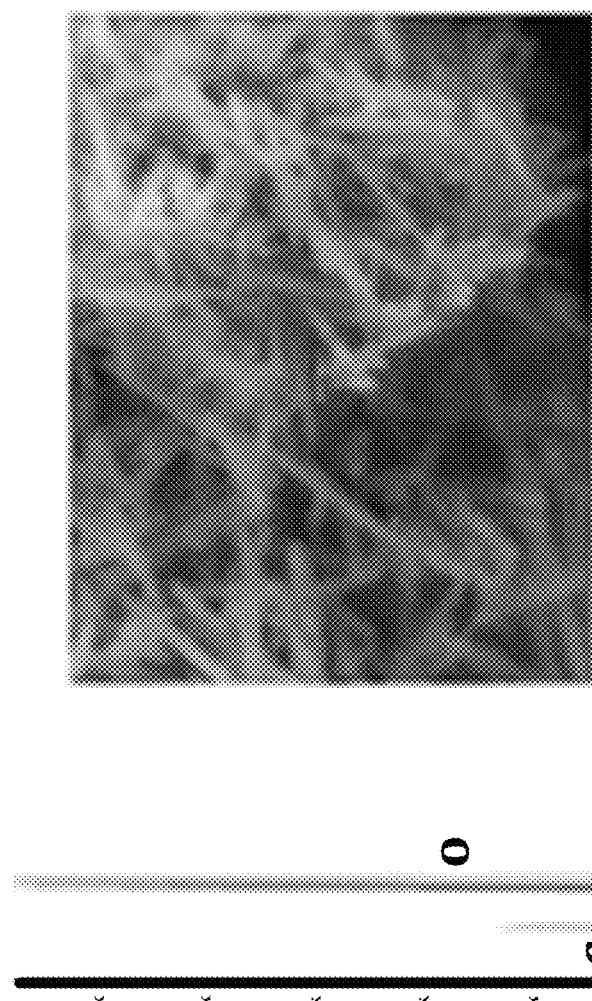
FIGS. 6a&b depicts SEM micrographs and EDX analysis of; (a) as-synthesized rare REM(HCOO)$_3$ crystals; (b) a rare earth metal oxide product after annealing.
Figure 6A:
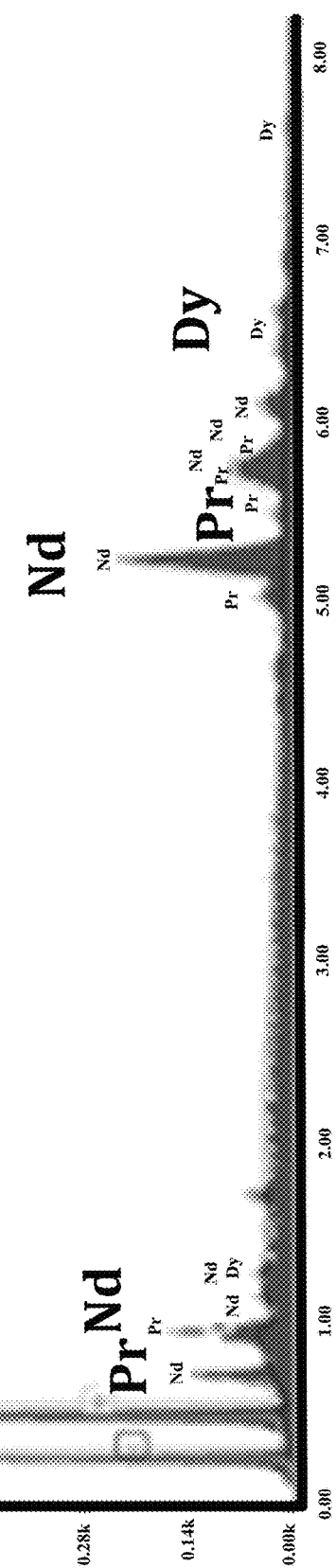
Figure 6B:
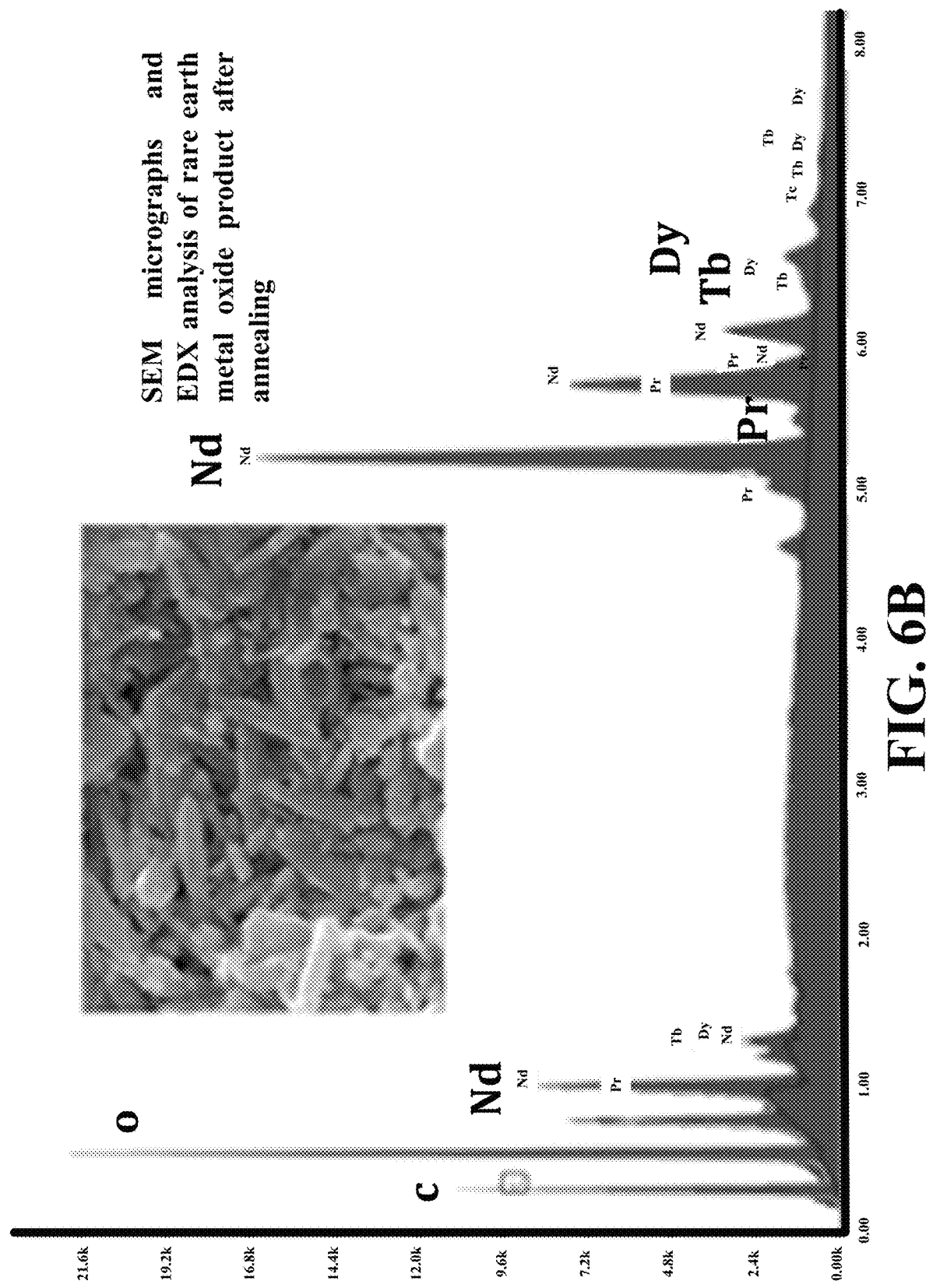

As a first example of the process, a 1:2:2 w/w of magnet materials to formic acid to water reaction mixture was used for the reaction. The reaction was performed at 100° C. for 24 h and the product was separated by a filtration method at room temperature. The final product phase of the reaction was a white/pale violet microcrystalline precipitate which was confirmed to be a mixture of rare earth metal formate (REM(HCOO)$_3$) and iron formate dihydrate (Fe(HCOO)$_2$.2H$_2$O) phases from the powder X-ray diffraction techniques as shown in FIG. 5.

Several methods such as washing with different solvents, magnetic separation and density separation were attempted to remove the impure iron formate phase from the rare earth formate phase. The most successful route was to wash the precipitate with excess amounts of water. As per the PXRD data shown in FIG. 5, the final product after excess water washing contained only a pure REM(HCOO)$_3$ product, confirming successful recovery of rare earths from NdFeB magnets materials.

When Fe$^{2+}$ oxidizes to Fe$^{3+}$, it forms nearly insoluble Fe(OH)$_3$, Fe(O)OH, and/or Fe$_2$O$_3$ phases. Thus, for a successful separation of Fe(HCOO).2H$_2$O, the iron formate phase needs to be fully removed. Any Fe(OH)$_3$ phase that forms is hard to separate from the REM(HCOO)$_3$ phase, and thus remains as an impurity phase in the final product. REM(HCOO)$_3$ purity will be significantly affected by Fe(OH)$_3$ formation, and is a previously known problem associated with the NdFeB magnet recycling techniques.

One alternative, is to carry out the final filtration step under an inert N$_2$ atmosphere and use deoxygenated water for the washing steps. This was more successful compared to the regular filtration.

Example 2

In a further example, the amount of formic acid and amount of water and solvent-to-solid ratios in the reaction mixture was systematically varied, with the intention of exploiting the substantial solubility difference between Fe(HCOO).2H$_2$O and REM(HCOO)$_3$. Excess amounts of water in the reaction mixture lowers the Fe(HCOO).2H$_2$O formation significantly, without affecting the REM(HCOO)$_3$ formation. When the amount of water increased substantially in the reaction mixture, the amount of Fe(HCOO).2H$_2$O was significantly reduced, or nearly absent from the final solid phase.

Based on the solubility data of Fe(HCOO).2H$_2$O, the required ratio of magnets to water to completely dissolve Fe(HCOO).2H$_2$O was calculated as about 1:30 w/w magnet materials to water at 25° C. Thus, by adding the appropriate amounts of water to the reaction mixture, Fe(HCOO).2H$_2$O formation can be substantially controlled. With this alteration of the process, the iron level in the final product was reduced between about 0.5% and about 0.8%, and the rare earth purity level improved to 99% or above.

Example 3

The detailed reaction scheme of the optimized process is as follows.

A ratio of magnet to formic acid was maintained at 1:2 w/w and a ratio of magnets to water was 1:30 w/w. Formic acid was used in a slightly excess amount over the theoretical amount to assist the reaction completion. The reaction temperature was set at 100° C.

The initial experiments were performed using 10 g of crushed magnets. The samples were mixed with 20 mL of 85% concentrated formic acid and diluted with 300 mL of water. The reactions were performed in a round bottom flask in an oil bath heated to 100° C. A vertically connected Liebig condenser was attached to the flask neck to cool and condense produced vapor. The condenser was used to minimize loss of water and formic acid during the boiling. The open end of the condenser was connected to gas bubbler to monitor hydrogen gas (H$_2$) evolution during the reaction.

As the reaction progressed, the magnet pieces dissolved in the solution and a white/greyish precipitate began to form and appear. Initial reactions were performed allowing 24 h reaction time to complete the reaction; subsequent experiments confirmed that within about 6 h of reaction, all of the rare earth metals from the magnet samples were dissolved by the reaction mixture. Throughout the reaction period, the amount of the solid precipitate in the reaction mixture increased as the portion of dissolvable components of the magnets dissolved.

Afterward, the mixture was cooled to room temperature, about 25° C. and filtered to separate the solid product from the liquid under suction.

Apart from the precipitate in the reaction mixture, parts of the protective Ni/Cu coating of the magnets were found to have remained unreacted with or undissolved by the formic acid/water mixture. These undissolved parts were easily removed using a magnetic stir bar retriever, but any other type of magnetic separator may be used including permanent or electromagnets or combination thereof. The precipitate was thoroughly washed with waster to remove any residual (Fe(HCOO)$_2$.2H$_2$O) adsorbed in the precipitate. The separation of any residual Fe(HCOO)$_2$.2H$_2$O from the product REM(HCOO)$_3$ may be achieved by washing the precipitate with excess amounts of water as the two solid materials have substantial different solubility in water. Fe(HCOO)$_2$.2H$_2$O is highly soluble in water, whereas the REM(HCOO)$_3$ is nearly insoluble in water. Thus, by using an excess amount of water, the residual Fe(HCOO)$_2$.2H$_2$O solid material can be completely removed from the solid product.

The white/greyish solid precipitate was confirmed as rare earth formate (REM(HCOO)$_3$). When an inadequate amount of water was used in the reaction, their formate dihydrate (Fe(HCOO)2.2H2O) phase may be observed in powder X-ray diffraction pattern.

After the removal of the residual Fe(HCOO)$_2$.2H$_2$O from the reaction mixture, the REM(HCOO)$_3$ phase was the only solid product remaining from the reaction mixtures. The final solid is dried under vacuum. The method resulted in REM(HCOO)$_3$ being recovered in high yield of at least 90%.

As the final step, REM(HCOO)$_3$ is annealed at 750° C. for 3 h in air to obtain the mixture of rare earth oxides, REM$_2$O$_3$/REM$_6$O$_{11}$ (REM include Nd, Pr, Dy, Tb) with a recovered yield of at least 90% in a purity of at least 99%. The purity of REM formate or oxides herein is measured relative to NREM formate or oxides in the relevant product.

The chemical analysis data of the final rare earth products phases have shown that the methods of this invention are capable of recovering at least 95% recovery efficiency for Nd, at least 95% recovery efficiency for Pr and at least 90% recovery efficiency for Dy and at least 85% recovery for efficiency for Tb.

The chemical analysis data of the final rare earth products phases have shown that the methods of this invention are capable of recovering rare earth formates in greater than 90% purity, for example about 99% purity compared to the non-rare earth formates.

REFERENCES CITED IN THE INVENTION

The following articles were cited above:
1. U.S. Department of Energy (2011) Critical Materials Strategy.
2. Constantinides, S (2013) The Demand for Rare Earth Materials in Permanent Magnets; Arnold Magnetic Technologies.
3. U.S. Bureau of Mines (1993) Recycling of Neodymium Iron Boron Magnet scrap.
4. Xu X, Chumbley L S and Laabs F S (2000) Liquid metal extraction of Nd from NdFeB magnet scrap. *Journal of Materials Research* 15(11): 2296-2304.
5. Zakotnik M, Devlin E, Harris I R, and Williams A J (2006) Hydrogen Decrepitation and Recycling of NdFeB-type Sintered Magnets. *Journal of Iron and Steel Research, International* 13(1): 289-295.
6. Itoh M, Miura K, and Machida K (2009) Novel rare earth recovery process on Nd—Fe—B magnet scrap by selective chlorination using NH4Cl. *Journal of Alloys and Compounds* 477: 484-487
7. Samarasekere P, Wang X, Kaveevivitchai W, and Allan J. Jacobson (2015) Reactions of Rare Earth Hydrated Nitrates and Oxides with Formamide: Relevant to Recycling Rare Earth Metals. *Crystal Growth & Design* 15(3): 1119-1128
8. Binnemans K, Jones P T, Blanpain B, Van Gerven T, Yang Y, Walton A, and Buchert M (2013) Recycling of rare earths: a critical review. *Journal of Cleaner Production* 51: 1-22 and references therein.
9. Bolotovskii R L, Bolotovskii R L, Bulkin Ap, Krutov G A, Turnov V A, Ul'yanov V A, Anston O, Hiismaki P, Poyry H, Tittla A, Loshmanov A A, and Furmanova N G (1990) Neutron diffraction study of the crystal structure of rareearth and yttrium anhydrous deuterated formates. *Solid State Communications* 76(8):1045-1049.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for recovering rare earth metals from waste magnets comprising:
    contacting a rare earth metal-containing magnet material with a reactant composition including a low molecular weight carboxylic acid and water under reaction conditions sufficient to dissolve or extract and concurrently precipitate rare earth metals from the rare earth metal-containing magnet material forming a rare earth metal precipitate including rare earth metal carboxylates and non-rare earth metal components, and
    removing the non-rare earth metal components from the rare earth metal carboxylates with water to form a purified rare earth metal carboxylate product,
    wherein the reaction conditions include at least a reaction temperature, a reaction pressure, a reaction time, and a stirring rate,
    wherein the reaction temperature is between about 25° C. and about 120° C.,
    wherein the reaction pressure is between about 1 atmosphere and about 5 atmospheres,
    wherein the reaction time is at least 24 hours, and
    wherein the stirring rate is at least 500 rpm.

2. The method of claim 1, further comprising the step of:
    prior to the contacting step, commutating the rare earth metal-containing magnet material to form a particulate rare earth metal-containing magnet material having an average particle size between about 10 nm and about 5 mm.

3. The method of claim 1, wherein the low molecular weight carboxylic acid is formic acid and a rare earth metal-containing magnet to formic acid to water ratio is between about 1.0:1.0:20 w/w to about 1.0:2.0:50 w/w.

4. The method of claim 3, wherein the rare earth metal-containing magnet material to formic acid to water ratio is between about 1:1.2:20 w/w/ and about 1:1.8:50 w/w.

5. The method of claim 4, wherein the rare earth metal-containing magnet material to formic acid to water ratio is between about 1.0:1.4:20 w/w and about 1.0:1.5:40 w/w.

6. The method of claim 5, wherein the rare earth metal-containing magnet material to formic acid to water ratio is about 1:1.44:30 w/w.

7. The method of claim 1, wherein:
    the reaction temperature is any discrete temperature in the range between about 25° C. and about 120° C.,
    the reaction pressure is ambient pressure,
    the reaction time is any discrete time period in the range between 3 hours and 24 hours, and
    the stirring rates any discrete stirring rate in the range between 100 rpm and 500 rpm.

8. The method of claim 1, wherein:
    the rare earth metals are selected from the groups consisting of Lanthanum (La), Cerium (Ce), praseodymium (Pr), neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbiium (Yb), Lutetium (Lu), and mixtures or combinations thereof; and
    the non-rare earth metals or elements (NREMs) are selected from the group consisting of iron (Fe), nickel (Ni), copper (Cu), other transition metals generally associated with materials that include REMs, boron (B), and mixtures or combinations thereof.

* * * * *